(12) United States Patent
Gömöri

(10) Patent No.: US 7,951,404 B2
(45) Date of Patent: May 31, 2011

(54) CONCENTRATE FOR PREPARING A DISINFECTANT AND METHODS FOR ITS PREPARATION AND USE

(75) Inventor: Janos Gömöri, Stäfa (CH)

(73) Assignee: Sanosil AG, Hombrechtikon (CH)

( * ) Notice: Subject to any disclaimer, the term of this patent is extended or adjusted under 35 U.S.C. 154(b) by 206 days.

(21) Appl. No.: 12/204,884

(22) Filed: Sep. 5, 2008

(65) Prior Publication Data
US 2010/0009010 A1     Jan. 14, 2010

(30) Foreign Application Priority Data
Jul. 11, 2008 (EP) .................................. 08104720

(51) Int. Cl.
| A01N 59/16 | (2006.01) |
| A01N 59/00 | (2006.01) |
| A01N 25/22 | (2006.01) |
| A61K 33/40 | (2006.01) |
| A61K 33/38 | (2006.01) |
| A61K 47/42 | (2006.01) |
| A61K 47/36 | (2006.01) |
| A61K 47/02 | (2006.01) |
| A61K 47/04 | (2006.01) |

(52) U.S. Cl. ........ 424/616; 424/618; 514/774; 514/782; 514/769

(58) Field of Classification Search .................. None
See application file for complete search history.

(56) References Cited

U.S. PATENT DOCUMENTS
| 4,009,252 A | * | 2/1977 | Izumi et al. .................. 423/584 |
| 4,915,955 A | | 4/1990 | Gomori |
| 5,437,858 A | | 8/1995 | Hungerbach et al. |
| 5,916,487 A | * | 6/1999 | Weidlich et al. .............. 252/586 |
| 5,945,032 A | | 8/1999 | Breitenbach et al. |
| 6,231,848 B1 | | 5/2001 | Breitenbach et al. |
| 7,351,684 B2 | | 4/2008 | Tichy et al. |
| 7,462,590 B2 | | 12/2008 | Tichy et al. |

FOREIGN PATENT DOCUMENTS
EP     524 150 A1     7/1992

OTHER PUBLICATIONS

Meier (Mutation Research 1988, 196, 211-245).*
Pastina et al. (J Phys Chem 1999, 103, 1592-1597).*
Linger et al. (Journal of the American Dental Association 2001, 132, 1287-1291).*
European Patent Office, European Search Report No. EP 08 10 4720, dated Sep. 29, 2008, 6 pages.

* cited by examiner

*Primary Examiner* — Johann R Richter
*Assistant Examiner* — Jessica Kassa
(74) *Attorney, Agent, or Firm* — Womble Carlyle

(57) ABSTRACT

A storage-stable aqueous concentrate for the preparation of a disinfectant and a disinfectant obtainable from such a concentrate by dilution are disclosed. The concentrate comprises hydrogen peroxide, colloidal silver, a biopolymeric stabilizer such as gum arabic, and phosphoric acid. In order to improve long-term stability and to reduce initial decomposition of the hydrogen peroxide in the first few days after preparing the concentrate, the concentrate further comprises sodium nitrate or sodium sulfate. The concentrate is free of any synthetic organic complexing agents, thus rendering the concentrate suitable for food- and drinking water applications. Also disclosed are methods of preparing and using the concentrate.

18 Claims, 1 Drawing Sheet

CONCENTRATE FOR PREPARING A DISINFECTANT AND METHODS FOR ITS PREPARATION AND USE

TECHNICAL FIELD

The present invention relates to an aqueous concentrate for preparing a disinfectant, to a disinfectant obtainable from such a concentrate by dilution with water, to a method of preparing such a concentrate, and to a method of use of such a concentrate or of a disinfectant obtained from the concentrate.

PRIOR ART

Contamination of drinking water and of water-carrying equipment such as ducts and tubes with infectious agents such as viruses, bacteria and fungi is a significant health problem throughout the world. Drinking water sanitation is especially important in health-sensitive environments such as hospitals, but may also be necessary on a large scale in extended drinking water systems, especially in the warmer regions of the world. Many approaches have been suggested to solve this problem, including the addition of halogens such as chlorine, bromine or iodine or of compounds releasing such halogens to the water. However, most of these methods are subject to environmental or health concerns themselves as they require the use of health-sensitive substances in sometimes very large amounts.

It has been suggested already a long time ago to utilize the oligodynamic properties of ionic silver compounds or of colloidal elemental silver in synergistic combination with the germicidal properties of hydrogen peroxide to prepare an efficient disinfectant that is, at least in principle, suitable not only for applications such as surface disinfection, but also for water sanitation. In this context, colloidal silver is preferred over ionic silver compounds due to its better pharmacological acceptability.

However, the stability of compositions comprising both hydrogen peroxide and colloidal silver is often not satisfactory. It is to be noted that long-term stability over periods of at least several months, typically even at least one or two years, is usually required for any commercially successful product. In this period of time, a product should not lose more than a few percent of its disinfecting or germicidal activity, even under adverse conditions such as elevated temperatures. At the same time, the product should not alter its appearance, i.e., it should remain clear at all times without any precipitation.

In the literature, a variety of stabilizers for aqueous solutions of hydrogen peroxide, in the absence of colloidal silver, have been described, including inorganic stabilizers such as phosphates, organic stabilizers and biopolymers, in particular, gelatin. However, in the presence of colloidal silver, such stabilizers alone usually do not achieve the required long-term stability. Complexing agents, in particular, chelating agents forming strong complexes with heavy metal ions may be added to counteract the adverse effect of silver ions to the stability of the hydrogen peroxide, thus improving long-term stability. However, such chelating agents usually are neither pharmacologically nor environmentally acceptable, in particular, for applications in drinking water sanitation or for food-related applications.

A particular problem with prior-art compositions comprising both hydrogen peroxide and colloidal silver is a relatively rapid decomposition rate of the hydrogen peroxide in a period lasting a few hours to a few days after initial mixing with the silver colloid, with decomposition slowing down thereafter. Sometimes this phenomenon can be observed as a kind of "bubbling" of the hydrogen peroxide solution in the first hours after mixing with the colloidal silver, very much like the sparkling of carbonated water. This behavior is not well understood and represents a major practical problem for manufacturers of disinfectants on the basis of colloidal silver and hydrogen peroxide. No solution to this problem seems to have been described in the prior art so far.

U.S. Pat. No. 4,915,955 to Gömöri discloses a concentrate containing either an ionic silver compound or colloidal silver, which, upon admixture with hydrogen peroxide, forms a disinfectant. Both the concentrate and the end product after admixture with hydrogen peroxide exhibit excellent long-term stability. Two examples are given in the patent. While in the first example, an ionic silver compound is used, the second example relates to a concentrate comprising colloidal silver. In this example, the colloid is stabilized by a hydrous polyhydroxyl monocarboxylic acid solution, which is known to form complexes with silver ions (see Römpp Chemie Lexikon, CD Version 1.0, Stuttgart/New York: Georg Thieme Verlag 1995, section "Hydroxycarbonsäuren"). Further organic compounds, in particular, alkali benzoates, were used as additional stabilizers. The concentrate was mixed with 50% hydrogen peroxide to obtain a concentrated disinfectant. While this ready-to-use disinfectant exhibits excellent efficacy and good stability, it is not free from environmental and toxicological concerns because of the presence of organic complexing agents and other organic stabilizers. In particular, the disinfectant does not comply with regulations for the sanitation of drinking water systems as currently in force in most developed countries.

U.S. Pat. No. 5,437,858 to Hungerbach et al. discloses a mouth-hygiene agent on the basis of a hydrogen-peroxide solution that is claimed to be "stabilized with colloidal silver". No details of the composition of this "stabilized" solution or of its preparation are disclosed.

U.S. Pat. No. 5,945,032 and U.S. Pat. No. 6,231,848 to Breitenbach et al. disclose disinfecting compositions comprising a polymer-bound hydrogen peroxide and a metal colloid, in particular, colloidal silver, which is additionally bound in the polymer. The polymer is preferably a homo- or copolymer of one or more N-vinyllactams. While these polymers are generally considered to be environmentally safe and pharmacologically acceptable in local applications, e.g., for the preparation of ointments to be locally applied or for coating air filters, their use in such large amounts as would be required for water sanitation is not free from environmental and pharmacological concerns.

U.S. Pat. No. 7,351,684 to Tichy et al. discloses a disinfectant comprising an organic peroxyacid, a peroxide and a transition metal, in particular, colloidal silver. While such disinfectants are claimed to include only food-grade ingredients, the presence of organic peroxyacids is undesirable in many food- and drink-related applications.

SUMMARY OF THE INVENTION

It is a first object of the present invention to provide a composition, in particular, a disinfectant or a concentrate for the preparation of such a disinfectant, the composition comprising both hydrogen peroxide and colloidal silver and showing good long-time stability while being free from environmentally and/or pharmacologically critical components such as synthetic organic complexing agents or organic peroxyacids, enabling the composition to be used in drinking-water applications or foodstuff-related applications.

It is a second object of the present invention to provide a composition comprising hydrogen peroxide and colloidal silver that has a long shelf life and does not exhibit the rapid initial decomposition after initial mixing of hydrogen peroxide and silver that has been observed in the prior art.

These and other objects are achieved by a concentrate having the features of claim 1. Thus, a storage-stable aqueous concentrate for the preparation of a disinfectant is provided, the concentrate comprising:

hydrogen peroxide in a concentration of 30-70% by volume (v/v) relative to the final concentrate;
colloidal silver in a concentration between 150 and 1000 ppm by weight (w/w) relative to the final concentrate;
a stabilizer comprising at least one biopolymer, the stabilizer having a concentration between 10 and 100 ppm by weight relative to the final concentrate; and
phosphoric acid in an amount effective to adjust the pH value of the concentrate to less than or equal to 3.0, preferably in a concentration of less than or equal to 500 ppm by weight relative to the final concentrate.

To inhibit decomposition of the hydrogen peroxide during storage of the concentrate, the concentrate comprises at least one sodium salt selected from the group consisting of sodium nitrate, sodium sulfate and combinations thereof, in an amount between 100 and 500 ppm by weight relative to the final concentrate. The concentrate is substantially free of any synthetic organic complexing agents forming complexes with silver, rendering it environmentally safe and pharmacologically acceptable.

Preferably, the concentrate consists essentially only of the above-mentioned components, i.e. of hydrogen peroxide, colloidal silver, of one or more biopolymers as stabilizer, phosphoric acid and the sodium salt. In this connection, the term "consisting essentially of" is to be understood as "consisting exclusively of", however, allowing for the presence of chemically inert materials that do not chemically interact with the other components, and/or allowing for the presence of traces of other substances, the trace amounts being side products from the production of the components of the concentrate, such side product being present in only very small concentrations in the range below, say, 10 ppm.

The terms "colloidal silver" or "silver colloid" are to be understood in the usual manner in the chemical art. In particular, these terms relate to any preparation of elemental silver that is sufficiently finely dispersed to form a colloid solution when dispersed in water. The mean particle size (arithmetic mean over the diameter of fictitious spheres having the same number of silver atoms) is generally in the range from 1 to 100 nanometers, typically 1 to 10 nanometers, corresponding to generally less than $10^9$ atoms per particle. Several different methods for the preparation of silver colloids exist, including, but not limited to, mechanical milling, electrolytic processes, and chemical reduction of silver salts in solution, and the invention is not limited to a silver colloid prepared by any particular method. The colloid can be provided in the form of a powder or of an aqueous dispersion ("colloid solution"). It is to be understood that colloidal silver may always also contain a certain proportion of ionic silver in addition to elemental silver due to redox reactions on the surface of the silver particles.

Importantly, the product is essentially free of any synthetic organic complexing agents, such as the polyhydroxyl monocarboxylic acids that were used in the prior art to stabilize the colloidal silver solution. This enables better compliance with drinking water regulations or food regulations as well as environmental regulations when the concentrate or the resulting disinfectant are used in the context of drinking water or food applications. The term "essentially free of synthetic organic complexing agents" is generally to be understood to mean that such agents are present at the most in trace amounts that are too low to bind any significant amount (less than a few percent, in particular, less than 5%, preferably less than 1%) of the silver present in the concentrate.

In addition to colloidal silver and hydrogen peroxide, the concentrate comprises phosphoric acid, a biopolymeric stabilizer, and sodium nitrate and/or sodium sulfate. While the stabilizing effects of phosphoric acid and of biopolymers such as gelatin are well known, it has now surprisingly been found that long-term stability is significantly improved if sodium nitrate or sodium sulfate is added to the concentrate, and, in particular, the initial decomposition of hydrogen peroxide is dramatically reduced. This effect was completely unexpected, and the mechanism by which these sodium salts act to stabilize the concentrate remains unknown at present.

Preferably, the sodium salt is sodium nitrate. The sodium salt is preferably present in an amount of 200 to 350 ppm by weight relative to the final concentrate. While higher or lower concentrations might still bring about positive effects, it has turned out that this range of concentrations brings about a good stabilizing effect with a minimum amount of sodium nitrate or sulfate. At too high concentrations, in particular, at concentrations much larger than 500 ppm w/w, undesired precipitates may form.

The amount of colloidal silver is preferably between 300 and 700 ppm by weight relative to the final concentrate. This range of concentrations has turned out to yield a high disinfecting activity in conjunction with hydrogen peroxide in concentrations in the range of 30% to 70% by volume. In particular, it is preferred that the hydrogen peroxide is present in a concentration of 45-55% by volume, most preferred approximately 50%, lower concentrations having a tendency to decay more quickly. Then the colloidal silver preferably has a concentration of about 450-550 ppm, most preferred about 500 ppm by weight. In more general terms, the numerical value of the content of colloidal silver, expressed in ppm by weight, amounts preferably to about eight to twelve times, most preferred about ten times, the numerical value of the concentration of hydrogen peroxide, expressed in percent by volume.

The biopolymeric stabilizer is preferably selected from the group consisting of gum arabic, gelatin, guar gum, carrageen and pectin. Such naturally occurring macromolecular biopolymers are sometimes designated in the literature as "protective colloids" that interact both with the hydrogen peroxide and the colloidal silver particles. They generally contain proteins, glycoproteins, polysaccharides or mixtures thereof.

Gum arabic is preferred. Gum arabic (E414, CAS 9000-01-05) is a natural gum that has been used for a long time in the food industry as a stabilizer and thickening agent. It is free from safety marking in the European Union according to directive 67/548/ECC. Gum arabic is commonly believed to consist of a complex mixture of polysaccharides and glycoproteins, in particular, to a rather large proportion of the alkaline earth salts and alkali salts of the so-called arabinic acid (polyarabinic acid), which designates a branched polysaccharide consisting of L-arabinose, D-galactose, L-rhamnose and D-glucuronic acid in a ratio of approximately 3:3:1:1. Gum arabic is mainly obtained from the barks of various acacia trees (mostly from Acacia Senegal or Acacia Seyal). Key advantages are that gum arabic is of non-animal origin, is perfectly edible and is thus perfectly acceptable in any food- or drink-related application. It has turned out that disinfecting compositions on the basis of colloidal silver and hydrogen peroxide, when stabilized with gum arabic, exhibit similar long-stability as such compositions stabilized with gelatin. Therefore, gum arabic may perfectly replace gelatin as a stabilizer in such disinfecting compositions.

The biopolymeric stabilizer, in particular, the gum arabic, need only be present in very small quantities. From an economic point of view, its content is preferably less than or equal to only 30 ppm by weight.

In the most preferred embodiment, the concentrate essentially consists of hydrogen peroxide in a concentration of 49-51% v/v, colloidal silver in a concentration of 490-510 ppm w/w, phosphoric acid in a concentration of 400-500 ppm w/w, sodium nitrate in a concentration of 250-300 ppm w/w, gum arabic in a concentration of 20-25 ppm w/w, and water (preferably deionized, ultrafiltered or treated by reverse osmosis), the water preferably having a conductivity of less than or equal to 0.1 µS/cm (microsiemens per centimeter). The conductivity is a direct measure for the content of foreign ions (ions other than $OH^-$ or $H_3O^+$ ions); any substantial ion content may decrease long-term stability, and in particular may lead to a tendency of the concentrate to precipitate.

In a different aspect, the present invention relates to a process for preparing a concentrate as described above and to a concentrate generally obtainable from such a process (i.e., having the same physical and chemical properties as a concentrate in fact obtained from the process) or actually obtained from the process. The process comprises the following steps:

(a) preparing an aqueous solution of a stabilizer comprising at least one biopolymer, the stabilizer preferably being gum arabic, in deionized water, preferably in a concentration of 2-20 g/l, more preferred 3-10 g/l;
(b) keeping said solution at a temperature less than or equal to 60° C. and adding phosphoric acid, preferably in a concentration between 50% and 90% by volume, to said solution while maintaining the temperature at less than or equal to 60° C., in a sufficient amount to obtain an acidified stabilizer solution at or below pH 3.0, the pH of the acidified stabilizer solution being preferably between 0.8 and 3.0;
(c) adding a sodium salt selected from the group consisting of sodium nitrate, sodium sulfate and combinations thereof, preferably in the form of an aqueous solution of said sodium salt, preferably in a concentration between 30 and 150 g/l, to said acidified stabilizer solution;
(d) adding an aqueous silver colloid solution, preferably in a concentration between 20 and 200 g/l, more preferred between 50 and 150 g/l, to the resulting solution to obtain an intermediate;
(e) homogenizing the obtained intermediate;
(f) adding said intermediate to an aqueous solution of hydrogen peroxide, preferably in a concentration between 30-70% by volume, more preferably 45-55%, at a temperature less than or equal to 30° C.; and
(g) homogenizing the resulting mixture to obtain said stable concentrate, in particular, by stirring for at least 120 minutes, more preferred at least four hours, at atmospheric pressure.

Preferably the step of homogenizing the intermediate comprises: agitating the intermediate at an increased pressure, in particular at a pressure between 1.5 and 3.0 bar, more preferred at a pressure of approximately 2 bar, for at least 60 minutes.

The invention further relates to an aqueous disinfectant comprising the concentrate of any of the preceding claims and water, preferably deionized, ultrafiltered or treated by reverse osmosis (RO), the concentration of the concentrate in the final disinfectant being at least 0.4% by weight. Again, the water is preferably of a purity resulting in a conductivity below 0.1 µS/cm in order to ensure sufficient long-term stability and to minimize the formation of precipitates. Preferably, the final disinfectant contains the concentrate in a concentration of at least 1%, more preferably at least 2% by weight.

In a further aspect, the invention provides a method of use of a concentrate as defined above or of a disinfectant comprising such a concentrate in a concentration of at least 0.5% by weight for the treatment of any material, in particular of any of the following:

potable water, e.g., drinking water;
equipment for storing or conveying potable water, e.g., installations such as tubings, armatures such as valves and faucets, tanks, boilers etc, in particular, in hospitals;
foodstuff or animal feeds;
foodstuff-related equipment such as food containers, cutlery, plates, kitchen equipment etc.;
sanitary equipment such as toilets, sinks etc.; or
human skin, in particular, the skin of the hand.

These methods may, in their simplest form, comprise the steps of preparing a disinfectant comprising the concentrate; and contacting the disinfectant with the material to be treated, preferably for at least 30 seconds.

BRIEF DESCRIPTION OF THE DRAWING

Preferred embodiments of the invention are described in the following with reference to the drawing, which shows in its only FIG. 1 a diagram representing the hydrogen peroxide content, $[H_2O_2]$, in percent by volume (v/v), of three different concentrates 1, 2 and 3 over a period of approximately one year (time t in days d).

DESCRIPTION OF PREFERRED EMBODIMENTS

Figure 1:
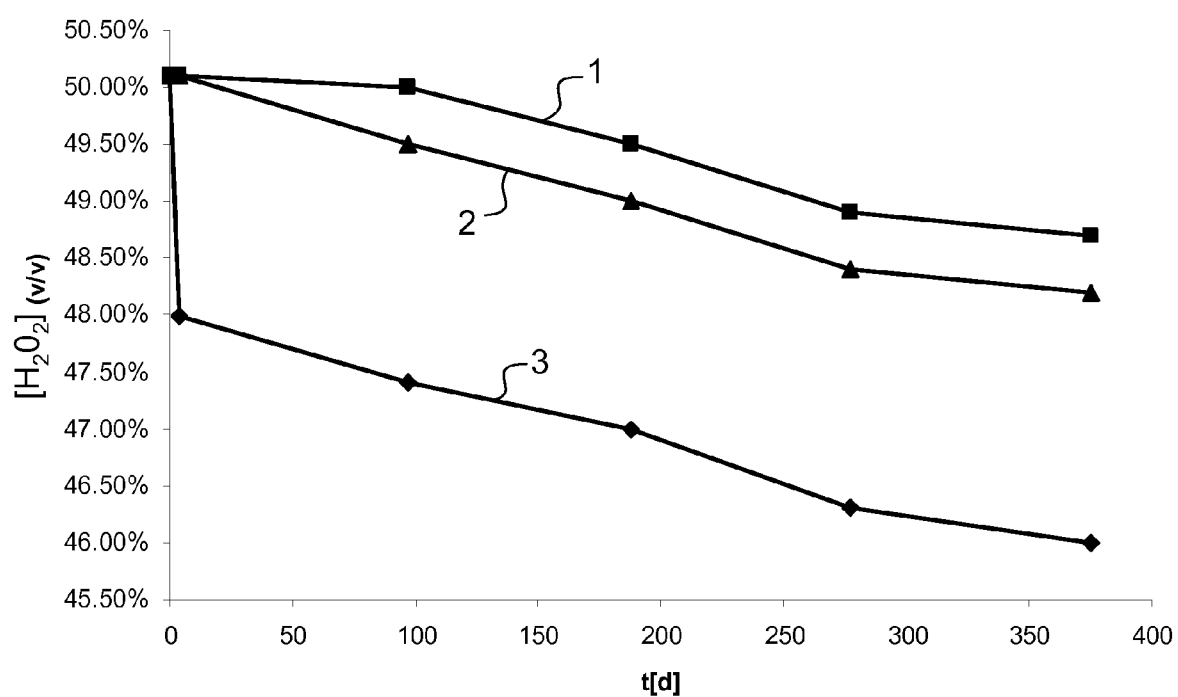

It is to be understood that the following examples are described for illustrative purposes only and not for the purpose of limiting the scope of the invention.

EXAMPLE 1

Preparation of a Concentrate Containing Sodium Nitrate 50 grams of a stabilizer (gum arabic "quick-gum type 8074", purified and standardized, E414/CAS 9000-01-05; Alfred L. Wolff, D-Hamburg) were dissolved in 950 ml of deionized water (conductivity at or below 0.1 µS/cm) at 55° C.; the mixture was filled into an agitator (stainless steel V2A or V4A, slow-running horseshoe mixer, heating and cooling facilities, pressure controllable up to 3 bar; passivated before use) and stirred for approximately 15 minutes. 400 ml of phosphoric acid (CAS 7664-38-2, 85%, purum; Fluka Chemie, CH-Buchs) were slowly added, yielding a pH of 1.2, and the resulting mixture was stirred for 30 minutes while the temperature was reduced to 50° C. 600 ml of an aqueous solution of sodium nitrate (CAS 7631-99-4, ultra pure; Fluka Chemie, CH-Buchs) were slowly added, and the resulting mixture was stirred during 30 minutes. 10,000 ml of aqueous colloidal silver (Argentum colloidale, CAS 7440-22-4, 120 g/l in purified water; Johnson Matthey, CH-Zurich) was added in portions, the pressure was increased to 2 bar, and the mixture was stirred for 120 minutes. The temperature was lowered to 30° C. The resulting storage-stable intermediate product (12 liters) was filled into standard containers made from HDPE (high-density polyethylene).

2,388 liters of aqueous hydrogen peroxide solution (CAS 7722-84-1, 49.0-49.9%, purum, Solvay, BE-Bruxelles) were filled into an agitator made from stainless steel V2A or V4A (resistant to hydrogen peroxide, sealable with pressure relief valve, passivated before use). 12 liters of the intermediate product were added in portions, and the resulting mixture was stirred for four hours. 2,400 liters of concentrate were thus obtained. The final content of sodium nitrate was 300 ppm w/w. The concentrate was filled into standard containers with pressure relieve valves.

EXAMPLE 2

Preparation of a Concentrate Containing Sodium Sulfate

A second concentrate was prepared as in example 1, wherein sodium nitrate was replaced by the same amount of sodium sulfate.

EXAMPLE 3

Preparation of a Concentrate without Sodium Salt

A concentrate was prepared as in example 1, however, without adding sodium nitrate, sodium sulfate or any other salts.

EXAMPLE 4

Stability Tests

The concentrates of Examples 1-3 were subjected to stability tests over a time of approximately one year. One liter of each concentrate was filled into a standard container with a pressure relieve valve (samples 1-3). The containers were stored together at temperatures between 20 and 25° C. The concentration of hydrogen peroxide was measured at days 0, 4, 97, 188, 277 and 375 after preparation of the concentrate. Measurements were performed oxidimetrically by the $KMnO_3$ method (permanganometry) in the usual manner. The results are shown in Table 1 and are represented in diagrammatic form in FIG. 1.

TABLE 1

| | Stability test | | |
|---|---|---|---|
| Days | Sample 1 (sodium nitrate) | Sample 2 (sodium sulfate) | Sample 3 (no salts) |
| 0 | 50.1% | 50.1% | 50.1% |
| 4 | 50.1% | 50.1% | 48.0% |
| 97 | 50.0% | 49.5% | 47.4% |
| 188 | 49.5% | 49.0% | 47.0% |
| 277 | 48.9% | 48.4% | 46.3% |
| 375 | 48.7% | 48.2% | 46.0% |

For sample 3, the concentration of hydrogen peroxide dropped from 50.1% to 48.0% within only four days. This rapid initial decomposition of hydrogen peroxide manifested itself in bubble formation starting immediately after mixing the intermediate product with the hydrogen peroxide solution. Thereafter, the hydrogen peroxide concentration decreased only slowly to 46% over a period of approximately one year.

In contrast, samples 1 and 2 did not exhibit any significant hydrogen peroxide decomposition in the first four days. After mixing the intermediate product with the hydrogen peroxide solution, no bubble formation was observed. Long-term stability was best for sample 1, containing sodium nitrate, with a loss of hydrogen peroxide concentration of only 1.4 percent points over a period of approximately one year. Thus sample 1 not only avoided initial decomposition of hydrogen peroxide, but also showed an unexpectedly high long-term stability. Sample 2, containing sodium sulfate, exhibited a slightly higher hydrogen peroxide loss of 1.9 percent points, comparable to that of sample 3 if the initial hydrogen peroxide decay in the first four days is disregarded, which is however still sufficient to be commercially attractive.

In summary, the addition of either sodium nitrate or sodium sulfate was able to prevent the rapid decay often observed after mixing colloidal silver preparations with hydrogen peroxide solutions. Additionally, the presence of sodium nitrate further improved long-term stability.

EXAMPLE 5

Virucidal Activity

Surface Test

Disinfectants obtained from the concentrate of example 1 were subjected to extensive tests for their virucidal, bactericidal and fungicidal activity (Examples 5 to 9).

For testing virucidal activity as a surface disinfectant, the concentrate was diluted with deionized water to obtain a final concentration of the concentrate in the disinfectant of 3% (Reagent A, corresponding to a concentration of hydrogen peroxide of approximately 1.5%) and of 6% (Reagent B, corresponding to a concentration of hydrogen peroxide of approximately 3%), respectively.

Virucidal activity was tested on a stainless steel surface against Poliovirus type I and Adenovirus type 5, following procedure according to EN 14476 (Phase 2, Step 1).

Reagents A and B were provided in sealed 1l containers. The reagents were kept in the dark until use. The reagents were used straight from the containers. Immediately before each experiment, an aliquot of 10 ml was retrieved using a sterile pipette and transferred to a sterile 12 ml reagent tube (Falcon, BD, USA). The reagents were pipetted from these tubes using sterile single use micropipetting filter tips (Eppendorf, Del.) equipped with an aerosol barrier.

Stocks of Adenovirus type 5, stem adenoid 75 were prepared according to standard in vitro infection protocols for cell culture. Virus titers were determined by cell infection using serial dilutions of the inoculum. The 50% tissue culture infectious dose (TCID50) was determined via cytopathic changes appearing in multiple parallel cultures. The stock used in the study had a TCID50 of $3 \times 10^{-8}$, reflecting a titer of $3 \times 10^8$ infectious units per milliliter.

Stocks of poliovirus type I, LSc2-ab were prepared according to standard protocols and characterized as above. The stock used in the study had a TCID of $2 \times 10^{-6}$, reflecting a titer of $10^6$ infectious units per milliliter.

A dry spot format for depositing the respective virus inoculum was chosen. A stainless steel surface (laminar flow bench, Skan A G, CH-Allschwil) was sterilized by standard procedures (UV treatment, wiping with a proven disinfectant, rinsing with sterile water and drying, wiping with 70% ethanol). Virus inocula (10 microliters volume each) were deposited in the form of spots on the surface using a micropipettor and were allowed to dry for 30 minutes. Spots of plain, virus free culture medium were applied in the same manner. The spots were covered with one of the reagents or with culture medium as controls. Spots were incubated for either 30 or 60 minutes.

Viruses were recovered by addition of 50 microliters of MEM to each spot. Virus infectivity was determined by standard methodology by in vitro infection of human RD-6 cells (Poliovirus) or of human HeLa cells (Adenovirus), respectively.

For Poliovirus, the results indicated a strong reduction of viral infectivity of ≧4 log 10 caused by both reagents. An exposure time of 60 minutes appeared to be sufficient for achieving this reduction for reagent A (3%), 30 minutes appeared to be sufficient for reagent B (6%).

For Adenovirus, the results indicated a strong reduction in infectivity by both reagents. An exposure time of 60 minutes appeared to be sufficient for achieving a reduction of viral infectivity of ≧3 log 10 for reagent A (3%); 60 minutes appeared to be sufficient for achieving a reduction of viral infectivity of ≧4 log 10 for reagent B (6%).

EXAMPLE 6

Virucidal Activity

In Vitro Tests

Further virucidal tests were performed according to EN 14675 (Phase 2, Step 1) in vitro against the following viruses: Bovine enterovirus type 1, ATCC VR-248 (family picornaviridae; RNS, unsheathed); Deparvac goose parvovirus strain (family parvoviridae; DNS, unsheathed); La Sota poultry pest virus strain (family paramyxoviridae; RNS, sheathed); Classic swine pest Alfort strain (family flaviviridae; RNS, sheathed); Gumboro disease GP-14 strain (family bimaviridae, RNS, unsheathed); and Aujesky virus (family herpesviridae, DNS, sheathed).

A disinfectant prepared by dilution with deionized water from a concentrate according to Example 1 was tested for three dilutions (concentrations of the concentrate according to Example 1 in the final disinfectant: 0.5%, 3.0% and 6.0%), at a temperature of 10° C. and for exposure times of 30 minutes, 1 hour and 3 hours. The disinfectant was added to a virus suspension in 3% BSA, diluted with hard water. The resulting mixture was incubated for the above-mentioned exposure times, and viral infectivity was determined by standard methods. In addition, standard validation experiments were performed (toxicity tests in the absence of virus suspension; comparative titration experiments; and reference inactivation tests with formaldehyde solution).

Test results indicated that the disinfectant was able to decrease virus infectivity by at least 4 log 10 for each of the above-mentioned viruses at all exposure times, if the concentration was at least 3.0%.

EXAMPLE 7

Bactericidal and Fungicidal Activity

Bactericidal and fungicidal activity of a disinfectant prepared from a concentrate according to Example 1 by dilution in deionized water to 3% final concentration were determined according to standards SN EN 1276 (Quantitative suspension experiment for determining bactericidal activity of chemical disinfectants; Phase 2, Step 1); SN EN 1560 (Quantitative suspension experiment for determining fungicidal activity of chemical disinfectants; Phase 2, Step 1), and SN EN 13697 (Quantitative surface experiment for determining bactericidal and/or fungicidal activity of chemical disinfectants; Phase 2, Step 2).

The suspension experiments were performed according to standard procedures for the following germs: *Escherichia coli*, ATCC 8739; *Aspergillus niger*, ATCC 9642; *Pseudomonas aeruginosa*, ATCC 9027; *Staphylococcus aureus*, ATCC 6538; and *Candida albicans*, ATCC 10231. The disinfectant exhibited a complete elimination of all tested germs except *Candida albicans* at all testing times (15, 30 and 60 minutes). For *Candida albicans*, a sufficient dispatch rate was achieved after a testing time of 60 minutes.

The surface disinfection experiments were performed for the same types of germs on aluminum plates at 21° C. The disinfectant showed a complete elimination of all tested germs (see above) at all testing times (15, 30 and 60 minutes).

EXAMPLE 8

Suitability as a Hand Disinfectant

Tests were performed for proving the suitability as a hand disinfectant according to norm SN EN 1500 (phase 2, step 2). Tests were performed for *Escherichia coli*, ATCC 8739. The tests were performed for a disinfectant prepared from a concentrate according to Example 1 by dilution in deionized water to 3% concentration. As a reference product, propan-2-ol was used in a concentration of 60% v/v. For the tests, 3 ml of the disinfectant and of the reference product, respectively, were applied twice to the hands of ten test persons. The application time was 60 seconds for eight of the persons and 30 seconds for two of the persons. No neutralization was performed. The disinfectant showed the same dispatch value of *E. coli* as the reference product. At an interaction time of 60 seconds, the disinfectant completely fulfilled the requirements of norm SN EN 1500.

What is claimed is:

1. A storage-stable aqueous concentrate for the preparation of a disinfectant, the concentrate comprising:
   hydrogen peroxide in a concentration between 30% and 70% by volume relative to the final concentrate;
   colloidal silver in a concentration between 150 and 1000 ppm by weight relative to the final concentrate;
   a stabilizer comprising at least one biopolymer, the stabilizer having a concentration between 10 and 100 ppm by weight relative to the final concentrate;
   phosphoric acid to adjust the pH value of the concentrate to less than or equal to 3; and
   at least one sodium salt selected from the group consisting of sodium nitrate, sodium sulfate and combinations thereof in an amount between 100 and 500 ppm by weight relative to the final concentrate,
   the concentrate being essentially free of any synthetic organic complexing agents.

2. The concentrate as claimed in claim 1, wherein the sodium salt is sodium nitrate.

3. The concentrate as claimed in claim 1, wherein the sodium salt is present in an amount of 200 to 350 ppm by weight relative to the final concentrate.

4. The concentrate as claimed in claim 1, wherein the amount of colloidal silver is between 300 and 700 ppm by weight relative to the final concentrate.

5. The concentrate as claimed in claim 1, wherein the amount of colloidal silver, numerically expressed in ppm by weight relative to the final concentrate, is between eight and twelve times the concentration of hydrogen peroxide, numerically expressed in percent by volume.

6. The concentrate as claimed in claim 1, wherein the stabilizer is selected from the group consisting of gum arabic, gelatin, guar gum, carrageen, pectin and combinations thereof.

7. The concentrate as claimed in claim 6, wherein the stabilizer is gum arabic.

8. The concentrate as claimed in claim 1, wherein the amount of the stabilizer is between 10 ppm and 30 ppm by weight.

9. The concentrate as claimed in claim 1, the concentrate essentially consisting of hydrogen peroxide in a concentration of 49-51% v/v, colloidal silver in a concentration of 490-510 ppm w/w, phosphoric acid in a concentration of 400-500 ppm w/w, sodium nitrate in a concentration of 250-300 ppm w/w, gum arabic in a concentration of 20-25 ppm w/w, and water.

10. An aqueous disinfectant comprising:
    water, and
    a concentrate comprising:
        hydrogen peroxide in a concentration between 30% and 70% by volume relative to the final concentrate;
        colloidal silver in a concentration between 150 and 1000 ppm by weight relative to the final concentrate;
        a stabilizer comprising at least one biopolymer, the stabilizer having a concentration between 10 and 100 ppm by weight relative to the final concentrate;
        phosphoric acid to adjust the pH value of the concentrate to less than or equal to 3; and
        at least one sodium salt selected from the group consisting of sodium nitrate, sodium sulfate and combinations thereof in an amount between 100 and 500 ppm by weight relative to the final concentrate,
        the concentrate being essentially free of any synthetic organic complexing agents,
    wherein:
        the concentrate is present in the disinfectant in a concentration of at least 0.4% by weight.

11. The disinfectant as claimed in claim 10, wherein the concentrate is present in a concentration of at least 2% by weight.

12. A method for treating drinking water, the method comprising:
    providing a disinfectant according to claim 10; and
    adding the disinfectant to drinking water.

13. A method for disinfecting a material, the method comprising:
    providing a disinfectant according to claim 10; and
    contacting the material with the disinfectant for at least 30 seconds.

14. A method for disinfecting equipment for storing or conveying potable water, the method comprising:
    providing a disinfectant according to claim 10; and
    contacting the equipment with the disinfectant for at least 30 seconds.

15. A method of preparing a storage stable aqueous concentrate, the method comprising:
    (a) preparing an aqueous solution of a stabilizer comprising at least one biopolymer;
    (b) keeping said solution at a temperature less than or equal to 60° C. and adding phosphoric acid to said solution while maintaining the temperature at less than or equal to 60° C. to obtain an acidified stabilizer solution at or below pH 3.0;
    (c) adding a sodium salt selected from the group consisting of sodium nitrate, sodium sulfate and combinations thereof to said acidified stabilizer solution;
    (d) adding an aqueous silver colloid solution to obtain an intermediate;
    (e) homogenizing the obtained intermediate;
    (f) adding said intermediate to an aqueous solution of hydrogen peroxide at a temperature less than or equal to 30° C.; and
    (g) homogenizing the resulting mixture to obtain said stable concentrate, wherein the concentrate is essentially free of any synthetic organic complexing agents.

16. The method of claim 15, the step of homogenizing the intermediate comprising agitating the intermediate at an increased pressure for at least 60 minutes.

17. The concentrate as claimed in claim 1, wherein the concentrate exhibits substantially no decomposition of hydrogen peroxide in the first four days after preparation of the concentrate.

18. The concentrate as claimed in claim 1, wherein the concentrate exhibits substantially no bubble formation the first four days after preparation of the concentrate.

* * * * *